United States Patent
Schwarz et al.

(10) Patent No.: US 7,153,888 B2
(45) Date of Patent: Dec. 26, 2006

(54) STABILIZATION OF BENZOYL PEROXIDE IN SOLUTION

(75) Inventors: Joseph Schwarz, Richmond Hill (CA); Michael Weisspapir, Richmond Hill (CA)

(73) Assignee: Alpharx Inc., Markham (CA)

( * ) Notice: Subject to any disclaimer, the term of this patent is extended or adjusted under 35 U.S.C. 154(b) by 0 days.

(21) Appl. No.: 11/016,711

(22) Filed: Dec. 21, 2004

(65) Prior Publication Data

US 2006/0135822 A1     Jun. 22, 2006

(51) Int. Cl.
*A61K 31/075* (2006.01)
*C07C 409/00* (2006.01)

(52) U.S. Cl. ..................... 514/714; 568/566
(58) Field of Classification Search ............ 562/3
See application file for complete search history.

(56) References Cited

U.S. PATENT DOCUMENTS

| | | | | |
|---|---|---|---|---|
| 3,887,652 A * | 6/1975 | Carrock et al. | ............... | 525/53 |
| 4,056,611 A | 11/1977 | Young | ............... | 424/62 |
| 4,640,932 A * | 2/1987 | Fong et al. | ............... | 514/714 |
| 4,725,429 A | 2/1988 | Scott et al. | ............... | 424/62 |
| 4,844,886 A | 7/1989 | Hartmann et al. | ............... | 424/62 |
| 4,923,900 A | 5/1990 | De Billez | ............... | 514/714 |
| 4,925,666 A | 5/1990 | Decker, Jr. et al. | ............... | 424/401 |
| 5,789,445 A * | 8/1998 | Schweiger | ............... | 514/568 |
| 6,433,024 B1 | 8/2002 | Popp et al. | ............... | 514/714 |

OTHER PUBLICATIONS

Vilen L Antonovskii , Sergei L Khursan, "Thermolysis of organic peroxides in solution", Russ. Chem. Rev., 2003, 72 (11), 939-963.
Zaman F, Beezer AE, Mitchell JC, Clarkson Q, Elliot J, Davis AF, Willson RJ. "The stability of benzoyl peroxide by isothermal microcalorimetry", Int J Pharm. Oct. 4, 2001; 227 (1-2): 133-7.
Zaman F, Beezer AE, Mitchell JC, Clarkson Q, Elliot J, Nisbet M, Davis AF. "The stability of benzoyl peroxide formulations determined from isothermal microcalorimetric studies". Int J Pharm. Aug. 28, 2001; 225(1-2): 135-43.
Chellquist EM, Gorman WG. "Benzoyl peroxide solubility and stability in hydric solvents". Pharm Res. Oct. 1992; 9 (10): 1341-6.
Das Gupta V. "Effect of some formulation adjuncts on the stability of benzoyl peroxide". J Pharm Sci. May 1982; 71 (5):585-7.
Bollinger JN, Lewis D, Mendez VM. "Benzoyl peroxide stability in pharmaceutical gel preparations". J Pharm Sci. May 1997; 66 (5):718-22.
Wenqiu Liu, Xuejun Liu, David Knaebel, Linda Luck, and Yuzhou Li. "Synthesis and Antibacterial Evaluation of Novel Water-Soluble Organic Peroxides Antimicrobial Agents and Chemotherapy", Apr. 1998, p. 911-915, vol. 42, No. 4.

* cited by examiner

*Primary Examiner*—Paul A. Zucker
(74) *Attorney, Agent, or Firm*—McCarthy Tetrault LLP

(57) ABSTRACT

The stabilization of benzoyl peroxide for extended periods of time is disclosed. The stabilized solution contains from between 0.5% and 20% organic peroxide and a stabilizer for preventing degradation of said peroxide in the solution.

13 Claims, 4 Drawing Sheets

STABILIZATION OF BENZOYL PEROXIDE IN SOLUTION

TECHNICAL FIELD OF THE INVENTION

The present invention relates to preparation of a stable solution of benzoyl peroxide, suitable for extended storage at room temperature.

FIELD OF INVENTION

The invention relates to the field of preparation of stable solutions of organic peroxide, for example, benzoyl peroxide (BP) and chemically related substances. Such stabilized organic peroxide solutions may be useful when oxidative properties of organic peroxide must be exploited, while chain reactions associated with radicals are suppressed. Benzoyl peroxide is water insoluble and this causes local irritation due to skin contact with crystalline benzoyl peroxide and visibly decreases its oxidative action. Benzoyl peroxide in solution is much more efficient than micronized BP suspensions for superficial treatment, but once dissolved, it becomes extremely unstable. Stabilization of BP in solution allows storage of such formulations for extended periods of time, and eases use of it for dermatological applications. Benzoyl peroxide's oxidative action enhances surface skin cleansing and disinfection, epithelial cell desquamation and an antibacterial and antifungal action.

BACKGROUND OF INVENTION

Organic peroxides are very unstable materials. Even in a dry crystalline state, organic peroxides decompose relatively fast (Ref. 1 and 2). The rate of thermal degradation increases exponentially with an increase of temperature. In solution, the rate of thermal degradation depends on the type of the solvent used, concentration of benzoyl peroxide solubility in the solvent system (Ref. 4). This compound is least stable in PEG 400. Stability is improved when water is added to PEG 400. Similar solvent effects can be observed in suspension. For benzoyl peroxide suspensions in PEG 400 and PEG 400/water blends, benzoyl peroxide stability is dependent on solubility, with improved stability occurring in blends where the benzoyl peroxide is least soluble. Thus, formulations of solubilized benzoyl peroxide in pharmaceutically acceptable solvents are unlikely to show good stability. However, suspension formulations should be reasonably stable if selected vehicle is provides low BP solubility (Ref. 4).

At 50° C. the potency of benzoyl peroxide suspension in polyethylene glycol ointment base decreases from 5% to less than 1% in 5 days. Benzoyl peroxide decomposes very quickly (first-order K value 0.028 day$^{-1}$ at 24° C.) in polyethylene glycol ointment base (Ref. 5).

Benzoyl peroxide is quite unstable in the presence of nucleophilic agents and certain acidic substances. BP is destroyed rapidly (within 1 month) in the presence of ethanol and acidic chelating agents, when stored at 30° C. or 40° C. (Ref. 6). An increase of the pH also dramatically accelerates degradation.

Organic peroxides are very strong oxidants. They can be used as radical initiators of polymerization, bleach agents and chemical etching components. Since peroxides easily react with different types of molecules such as unsaturated compounds, amines and amino acids, proteins, dyes, oils, thiols, etc., it is difficult to obtain stabilized peroxide solutions. The stability of peroxides in solution is inversely related to their solubility in the solvent system—i.e. the less of peroxide is in dissolved state, the more stable is the preparation (Refs. 1 and 4).

Peroxides possess strong antibacterial properties (Ref. 7). A higher stability of peroxides prevents the undesirable degradation and leads to a longer-lasting antimicrobial effects.

Attempts at stabilizing benzoyl peroxide in solution using different stabilizers, such as chelating agents, pH adjusters, solvent mixtures and other additives (acetanilide, benzoic acid, chlorhydroxyquinoline, and hydroxyquinoline) have not been successful (Ref. 5 and 6). Addition of chlorhydroxyquinoline slightly improves stability, but this improvement is not significant enough to provide a solution, stable for more than 1 month at room temperature.

In U.S. Pat. No. 4,844,886, Hartmann and Kohler use bisabolol to stabilize hydrogen peroxide in an emulsion-surfactant system. However this approach is not suitable for water-insoluble organic peroxides.

Benzoyl peroxide is one of the most widely used compounds for acne treatment due to significant antimicrobial activity, mild keratolytic and duct opening properties and low cost. The actions include a topical antimicrobial effect against infecting bacteria, the removal of the horny layer of the epidermis, as well as the removal of thickened sebum and other debris clogging follicular pores.

Benzoyl peroxide, especially in suspensions, has the potential to irritate the skin when applied at concentrations suitable for effective acne treatment. Formulations combining commonly used surfactants such as sodium laurylsulfate with BP, may exaggerate this irritating effect. To decrease irritability, moisturizers and emollients are often used in combination with mild non-ionic surfactants. U.S. Pat. No. 4,056,611, describes compositions containing a non-ionic surfactant, a short chain of alcohol and water. In U.S. Pat. No. 4,725,429, Scott et al., present a composition of benzoyl peroxide in silicon oil, combined with surfactants and high-alkyl alcohols to provide increased bioavailability due to the occlusive properties of the vehicle.

The extremely low solubility of benzoyl peroxide in a water medium has motivated investigators to develop solubilized formulations, which provide a high concentration of the oxidizer at the point of action, i.e. clogged follicle or blemish spot.

U.S. Pat. No. 4,923,900, discloses compositions containing BP, water and a water-miscible solvent with a boiling point higher than that of water. Dimethylisosorbide is indicated as a particularly useful solvent in the disclosed compositions. The disclosed compositions are indicated for the treatment of skin conditions such as acne and seborrhea, dermatophyte infection, reactions to irritative plant contactants such as the oleoresins of poison ivy and in the prevention of the development of offensive body odour. Nevertheless, in formulations prepared according to U.S. Pat. No. 4,923,900, only a small percentage of the BP remains in a dissolved state, explaining why the treatment efficacy is much lower than would be indicated for a totally dissolved oxidant.

Few examples of solubilized benzoyl peroxide formulations exist. Decker et al. in U.S. Pat. No. 4,925,666, describe a solubilized benzoyl peroxide formulation in polymeric siloxanes at elevated temperature.

Benzoyl Peroxide forms clear solutions, but requires high concentrations of volatile organic solvents such as acetone and isopropyl alcohol to achieve this. The solutions obtained must be stored under refrigeration. Evaporation of the solvent after application of the solution to the epidermis may cause crystallization of the drug on the skin surface.

Popp and Stiefel in U.S. Pat. No. 6,433,024, disclose a composition of benzoyl peroxide in a vehicle comprising isosorbide ester and water and containing surfactants, hydroxyacids and polyvinylpyrrolidone carboxylate to improve solubility and decrease irritation. None of the known currently available topical formulations of BP possesses the optimal combination of effective anti-acne properties, a non-irritating composition and a formulation stability that provides for efficacious treatment of acne conditions and satisfactory long-term storage stability at an elevated temperature. There remains a need for a stable formulation of solubilized BP to increase treatment efficacy and to decrease skin irritability.

SUMMARY OF THE INVENTION

An objective of the present invention is to provide a solution of organic peroxide, e.g. benzoyl peroxide, which remains stable when stored at ambient temperature for an extended period of time.

Another objective of the present invention is to provide a non-volatile solvent composition, which allows benzoyl peroxide or other organic peroxides to be dissolved in concentrations high enough to provide efficacy in anticipated applications with minimal skin irritating properties.

A further objective of the present invention is to provide a stabilized solution of organic peroxide, which contains from 0.5 to 20% of organic peroxide for preventing degradation of said organic peroxide content in said solution.

Yet another objective of the present invention is to provide a stabilized solution of organic peroxide comprising organic peroxide in an amount from 0.5% to 20% and an antioxidant in an amount from between 0.01% to 10%, the solution being stabilized from degradation of the organic peroxide contact in the solution.

Having thus generally described invention, reference will now be made to the accompanying drawings.

DETAILED DESCRIPTION OF PREFERRED EMBODIMENTS

Figure 1:
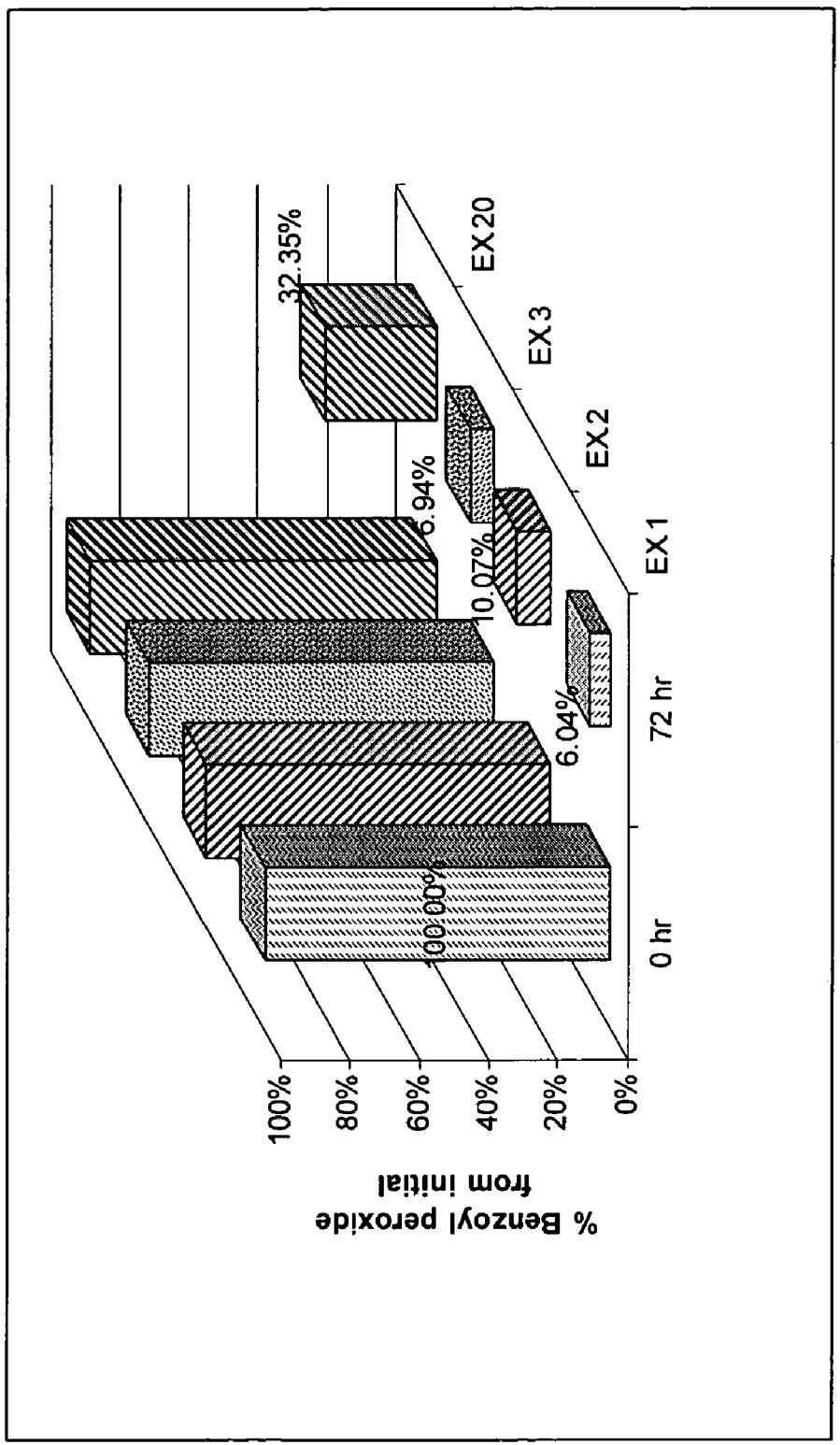
FIG. 1 is a graphical representation of stability data for benzoyl peroxide solutions.

The present invention relates to a preparation of homogenous solution of organic peroxide, preferably benzoyl peroxide, and this solution remains stable for several months at room temperature. Peroxide degradation in this solution does not exceed 10% per year from the initial concentration under storage in ambient conditions. The peroxide compound remains solubilized without crystallization or precipitation.

Benzoyl peroxide in solution has visible advantages when compared to existing formulations of suspended milled or micronized material. It works much more effectively as oxidizer and causes less irritation when applied to the skin, since no crystalline precipitate occurs. Superior skin penetration properties are also demonstrated. Nevertheless, there are serious obstacles in obtaining BP in a dissolved state. First, the solubility of BP in most solvents is relatively low, usually below 20 mg/ml for common solvents such as alcohol, PEG and propylene glycol. Further, dissolution of BP in a suitable solvent accelerates the irreversible degradation of the peroxide. In different solvents, half-life (50% content decrease) at room temperature for pure BP may vary from 6.3 to 266 days (Ref. 4). Moreover, if the solvent is water miscible, significant precipitation occurs when the water concentration increases. The solubility drops 2–4 orders of magnitude, while the water content grows from 0 to 25%. Additionally, evaporation of volatile solvents may also trigger precipitation and crystallization of peroxide, leading to possible local skin irritation from contact with precipitated peroxide crystals.

As previously stated, solutions of benzoyl peroxide in polar solvents are extremely unstable and there are no available data in the literature describing the successful stabilization of such solutions.

It was surprisingly found that addition of certain antioxidants to a solution of benzoyl peroxide dramatically improves the stability of the solution. The degradation rate is decreased 100–1000 times and the solutions thus obtained can be stored at room temperature for extended periods of time without significant loss of active peroxide content.

Solutions of benzoyl peroxide in different solvents and combinations thereof—in ethyl alcohol, propylene glycol, liquid polyethylene glycol PEG-400, dimethylisosorbide and ethoxydiglycol were investigated. The prepared solutions of benzoyl peroxide were placed into tightly closed glass vials and stored in chambers with controlled temperature and humidity. Concentrations of benzoyl peroxide were tested using iodine-thiosulfate titration method. Initial concentration of benzoyl peroxide was in the range of 2% through 10% by weight.

The following examples are intended to illustrate certain preferred embodiments of the invention and no limitation upon the invention is implied by their inclusion.

EXAMPLES 1–20

Compositions of examples 1 through 20 are presented in tables 1 and 2.

EXAMPLES 21–46

Examples 21 through 39 are similar to composition of example 18, but contain as the antioxidant 0.1% of either Rutoside, Cystine, Biotin, Pyridoxine, Coniferyl alcohol, Acetylcysteine, oxidized glutathion, pyrocatechine, propylgallate, butylparaben, propylparaben, ascorbyl palmitate, dry green tea extract, reseveratrol, quercetin, ubiquinone, pyridoxine, acetylpantotenate, butylated hydroxyanisole, beta-ionol, 8-hydroxyquinoline, hydroquinone, creatinine, naphtoquinone, turmeric extract (curcumin) or superoxide dismutase.

Figure 2:
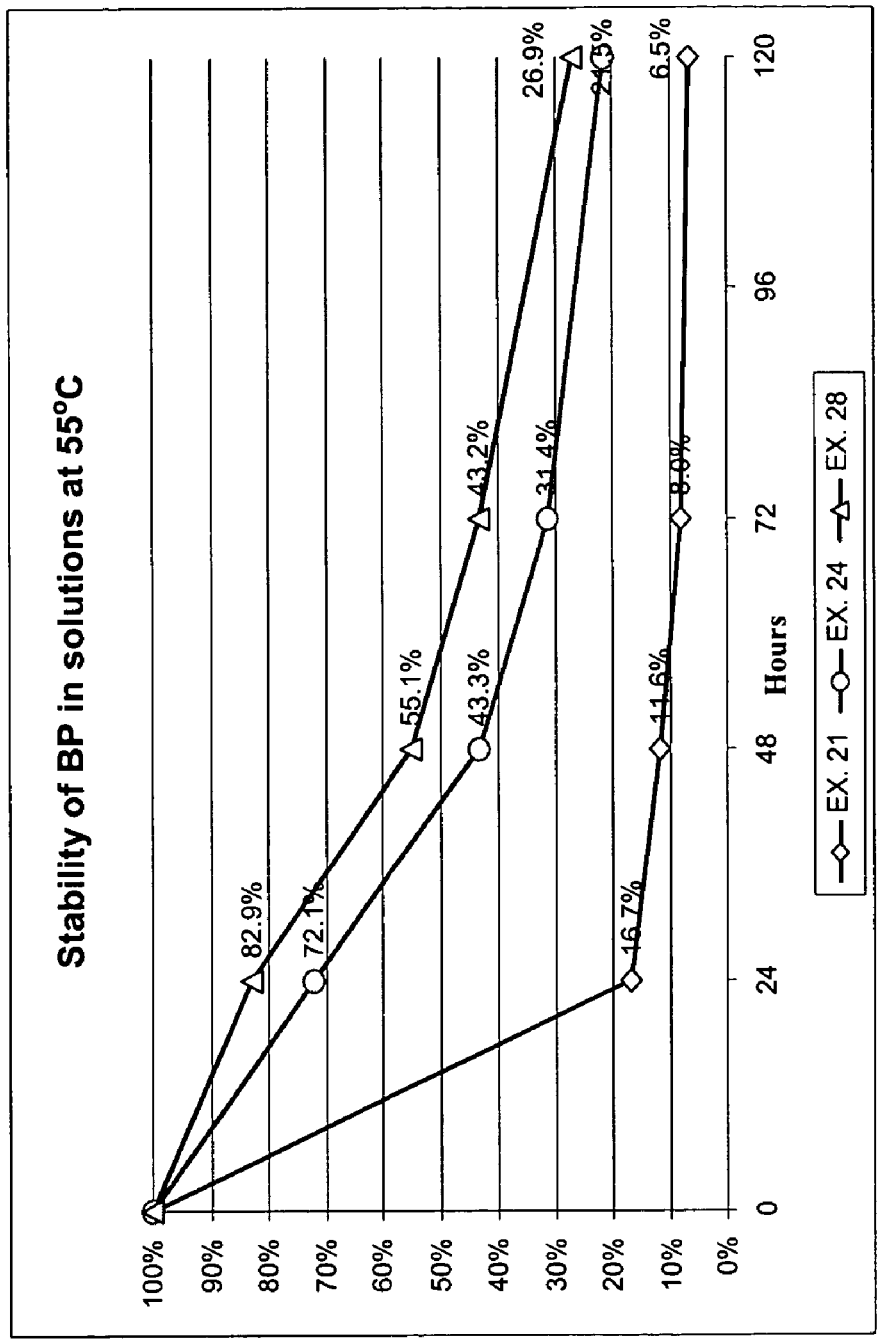
FIG. 2 is a graphical representation illustrating comparative data for various benzoyl peroxide solutions.
Figure 3:
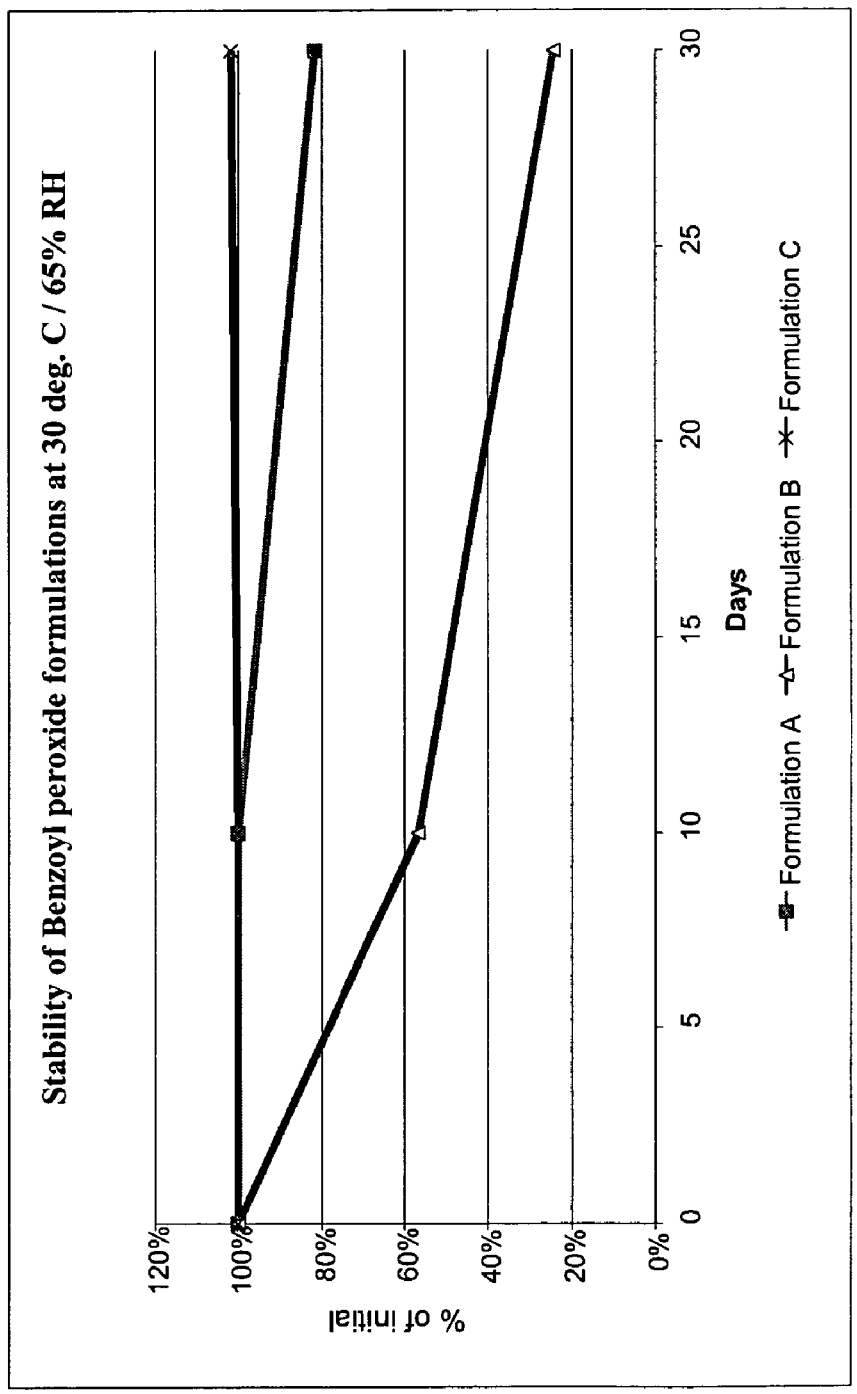
FIG. 3 is a graphical representation illustrating comparative data for various benzoyl peroxide semisolids.
Figure 4:
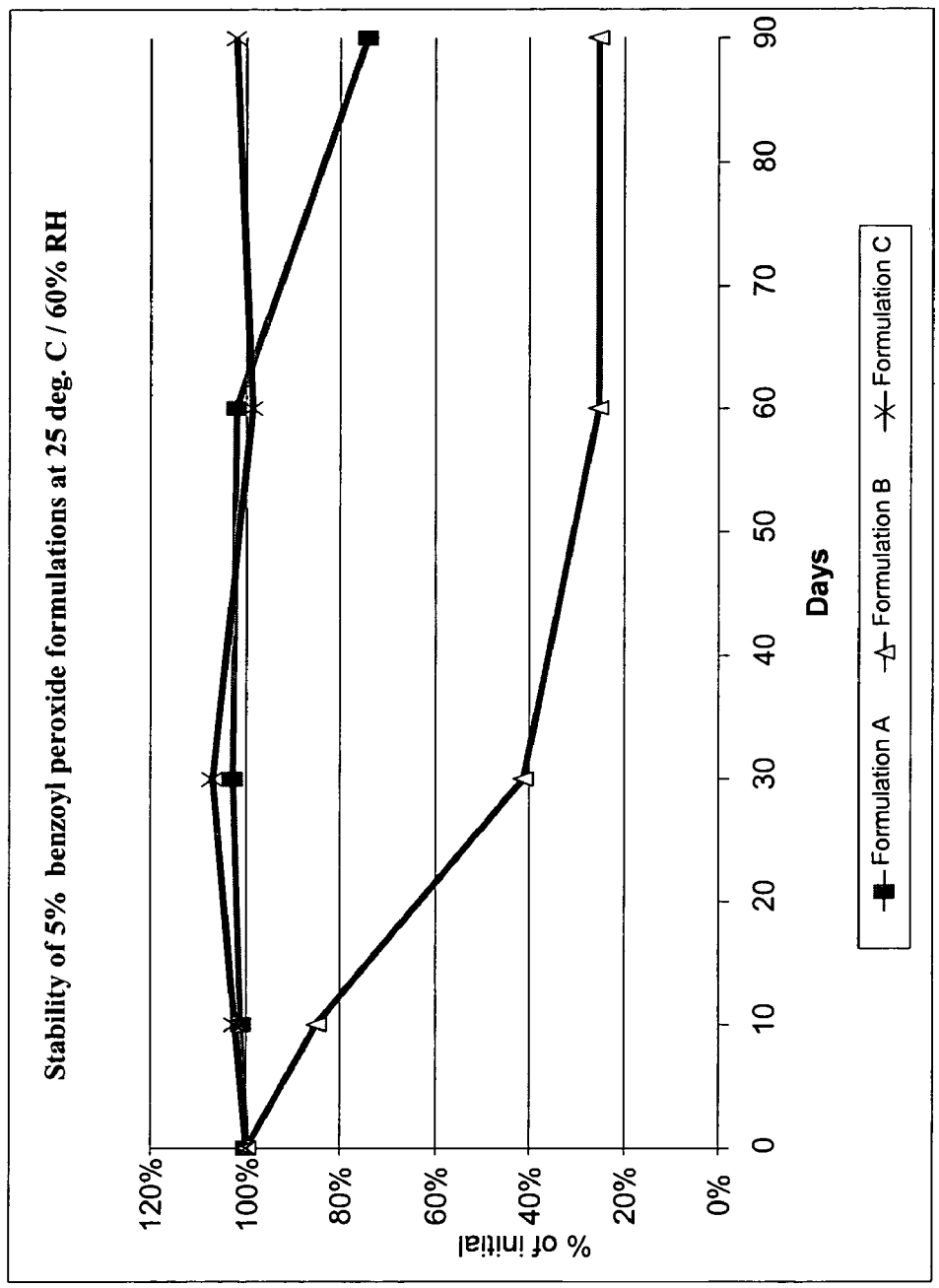
FIG. 4 is a graphical representation illustrating comparative data for various benzoyl peroxide semisolids at 25° C.

FIGS. 1 through 4 represent stability data for some of the prepared solutions. It is clear that addition of an antioxidant significantly suppresses the degradation of benzoyl peroxide in dissolved state for a much longer period if compared with composition having no antioxidants added. Semisolid preparations containing dissolved benzoyl peroxide show a high stability in different temperature and humidity environments. Such formulations may be used in making dermatological, cosmetic, toiletry and personal care products with increased efficacy. The addition of an antioxidant to such solutions provides a stable benzoyl peroxide in a dissolved state.

TABLE 1

Compositions of benzoyl peroxide solutions (examples 1–10)

| | EX. 1 | EX. 2 | EX. 3 | EX. 4 | EX. 5 | EX. 6 | EX. 7 | EX. 8 | EX. 9 | EX. 10 |
|---|---|---|---|---|---|---|---|---|---|---|
| BZP (75%) | 1 | 1 | 0.9 | 0.5 | 0.5 | 0.5 | 0.5 | 0.5 | 0.5 | 0.5 |
| Ethoxydiglycol | 19 | | 8 | 9.4 | | | | | | |
| Dimethylisosorbide | | 19 | | | 9.4 | 9.4 | 9.4 | 9.4 | 9.4 | 8.5 |
| Ethanol | | | 9.1 | | | | | | | |
| Citric acid | | | | 0.01 | 0.01 | | | | | |
| Thioctic acid | | | | | | 0.01 | | | | |
| Tocopherol succinate | | | | | | | 0.01 | | | |
| Mix Tocopherols | | | | | | | | 0.01 | | |
| Squalene | | | | | | | | | 0.01 | |
| Salicylic acid | | | | | | | | | | 0.1 |
| Total | 20 | 20 | 18 | 10 | 10 | 10 | 10 | 10 | 10 | 10 |

TABLE 2

Compositions of benzoyl peroxide solutions (examples 11–20)

| | EX. 11 | EX. 12 | EX. 13 | EX. 14 | EX. 15 | EX. 16 | EX. 17 | EX. 18 | EX. 19 | EX. 20 |
|---|---|---|---|---|---|---|---|---|---|---|
| BZP (75%) | 0.5 | 0.5 | 0.5 | 0.5 | 0.5 | 0.5 | 0.5 | 0.5 | 0.5 | 0.5 |
| Dimethylisosorbide | 9.4 | 9.4 | 9.4 | 9.4 | 9.3 | 8.3 | 9.4 | 9.4 | 9.1 | 8.1 |
| Thioctic acid | | | | | | | | | 0.1 | 0.1 |
| Salicylic acid | | | | | | 0.1 | | | | 0.1 |
| Butylated Hydroxytoluene | 0.01 | | | | 0.01 | 0.01 | | | 0.1 | 0.1 |
| Ascorbyl Tetrapalmitate | | 0.01 | | | | | | | | |
| Resorcinol | | | 0.01 | | 0.1 | 0.1 | | | 0.1 | 0.1 |
| Thymol | | | | 0.01 | | | | | | |
| Rosemary terpenes | | | | | | | | 0.1 | | |
| Bisabolol | | | | | | | | 0.1 | 0.1 | 0.1 |
| Total | | 10 | 10 | 10 | 10 | 10 | 10 | 10 | 10 | 10 |

TABLE 3

Compositions of benzoyl peroxide solutions (examples 21–30)

| | EX. 21 | EX. 22 | EX. 23 | EX. 24 | EX. 25 | EX. 26 | EX. 27 | EX. 28 | EX. 29 | EX. 30 |
|---|---|---|---|---|---|---|---|---|---|---|
| BZP (75%) | 0.5 | 0.5 | 0.5 | 0.5 | 0.5 | 0.5 | 0.5 | 0.5 | 0.5 | 0.5 |
| Dimethylisosorbide | 5 | 5 | 5 | 5 | 5 | 5 | 5 | 5 | 5 | 5 |
| Ethoxydiglycol | 3 | 3 | 3 | 3 | 3 | 3 | 3 | 3 | 3 | 3 |
| Butylated Hydroxytoluene | | | | | 0.1 | 0.1 | 0.1 | 0.1 | 0.1 | 0.1 |
| Resorcinol | | | | | | | 0.2 | | | 0.2 |
| Rutoside | 0.01 | | | 0.01 | 0.01 | 0.01 | 0.01 | 0.01 | 0.25 | 0.01 |
| Salicylic acid | | | | | | | | 0.1 | 0.1 | 0.1 |
| Thioctic acid | | | | 0.02 | 0.02 | 0.05 | 0.05 | 0.05 | 0.05 | 0.5 |
| Biotin | | 0.02 | | | | | | | | |
| Cystine | | | 0.02 | | | | | | | |
| Total | 8.7 | 8.52 | 8.52 | 8.9 | 9 | 9.3 | 9.5 | 10.3 | 10.6 | 10.5 |

We claim:

1. A stabilized solution of organic peroxide in a non-volatile solvent, comprising from 0.5–20% of organic peroxide and a radical scavenger antioxidant stabilizer for preventing degradation of said organic peroxide content in said solution and a non-volatile solvent, wherein said organic peroxide is completely dissolved in the non-volatile solvent, and wherein said stabilizer is selected from the group consisting of: butylated hydroxytoluene, butylated hydroxyanisole, propylgallate, thymol, resorcinol, methylresorcinol, resveratrol, pyrocatechol, pyrogallol, propylgallate, thioctic acid, salicylic acid, salicylates, tyrosine, biotin, acetylcysteine, methionine, acetyltyrosine, oxidized glutathione, coniferyl alcohol, vitamin E and derivatives thereof, vitamin C and derivatives thereof, beta-carotene and carotenoids, vitamin A and derivatives thereof, vitamin B and derivatives thereof, vitamin K and derivatives thereof piridoxine, ubiquinone, creatine, creatinine, squalene, bisabolol, flavonoids, antocyanes, phthalocyanes, rutin, curcumin, quercetin and superoxide dismutase.

2. The solution as set forth in claim 1, wherein said organic peroxide is benzoyl peroxide.

3. The solution as set forth in claim 1, wherein said stabilizer is present in an amount from 0.01 to 10% for stabilizing said solution.

4. A stabilized solution of organic peroxide comprising:
a non-volatile solvent,
an organic peroxide in an amount from 0.5% to 20%; and
an antioxidant in an amount from between 0.01% to 10%, wherein said organic peroxide is dissolved in said non-volatile solvent said solution being stabilized from degradation of said organic peroxide contact in said solution, such tat the solution retains more than 90% of initial peroxide content alter 30 days storage at 30 degrees Celsius.

5. The solution as set forth in claim 1 wherein the solution contains no crystalline peroxide material.

6. A solution as set forth in claim 1, wherein said non-volatile solvent is selected from the group consisting of: propylene glycol, butylenes glycol, polyethylene glycols, ethoxydiglycol, isosorbide esters, dimethylisisorbide, diethylisosorbide, methylethylisosorbide, dimethylformamide, ethylacetate, N-methylpyrrolidone.

7. A solution as set forth in claim 6, wherein said non-volatile solvent is selected from the group consisting of polyethylene glycol, ethoxydiglycol, dimethylisosorbide or mixture thereof.

8. The solution as set forth in claim 4 wherein the solution contains no crystalline peroxide material.

9. A solution as set forth in claim 4, wherein said non-volatile solvent is selected from the group consisting of: propylene glycol, butylenes glycol, polyethylene glycols, ethoxydiglycol, isosorbide esters, dimethylisisorbide, diethylisosorbide, methylethylisosorbide, dimethylformamide, ethylacetate, N-methylpyrrolidone.

10. A solution as set forth in claim 9, wherein said non-volatile solvent is selected from the group consisting of polyethylene glycol, ethoxydiglycol, dimethylisosorbide or mixture thereof.

11. The solution as set forth in claim 4, wherein said organic peroxide is benzoyl peroxide.

12. The solution as set forth in claim 4, wherein the antioxidant is selected from the group consisting of monophenols, di-phenols, tri-phenols and polyphenols, hydroxyaromatic acids, catecholes, substituted phenols, unsaturated compounds, sulfides, disulfides and other sulphur containing compounds, precipitated sulphur, aminoacids, tocopherols, toeotrienols, isoprenoids, terpenes, polyeues, and catecholes.

13. The solution as set forth in claim 4 wherein said antioxidant is selected from the group consisting of butylated hydroxytoluene, butylated hydroxyanisole, propylgallate, thymol, resorcinol, methylresorcinol, resveratrol, pyrocatechol, pyrogallol, propylgallate, thioctic acid, salicylic acid, salicylates, tyrosine, biotin, acetylcysreine, methionine, acetyltyrosine, oxidized glutathione, coniferyl alcohol, vitamin E and derivatives thereof, vitamin C and derivatives thereof, beta-carotene and carotenoids, vitamin A and derivatives thereof, vitamin B and derivatives thereof, vitamin K and derivatives thereof, piridoxine, ubiquinone, creatine, creatinine, squalene, bisabolol, flavonoids, antocyanes, phthalocyanes, rutin, curcumin, quercetin and superoxide dismutase.

* * * * *